US009315796B2

(12) United States Patent
Kim et al.

(10) Patent No.: US 9,315,796 B2
(45) Date of Patent: Apr. 19, 2016

(54) METHOD FOR ACTIVATING CATALYST USING PHOTOTHERMAL NANOMATERIALS

(75) Inventors: Min Gon Kim, Daejeon (KR); Taihua Li, Daejeon (KR); Yong Beom Shin, Daejeon (KR)

(73) Assignee: Korea Research Institute of Bioscience and Technology, Daejeon (KR)

( * ) Notice: Subject to any disclaimer, the term of this patent is extended or adjusted under 35 U.S.C. 154(b) by 513 days.

(21) Appl. No.: 13/817,305

(22) PCT Filed: Aug. 18, 2011

(86) PCT No.: PCT/KR2011/006099
§ 371 (c)(1),
(2), (4) Date: Apr. 5, 2013

(87) PCT Pub. No.: WO2012/023820
PCT Pub. Date: Feb. 23, 2012

(65) Prior Publication Data
US 2013/0210115 A1    Aug. 15, 2013

(30) Foreign Application Priority Data

Aug. 18, 2010  (KR) .................. 10-2010-0079606
Aug. 18, 2011  (KR) .................. 10-2011-0082306

(51) Int. Cl.
| | |
|---|---|
| *B82Y 30/00* | (2011.01) |
| *C12N 9/96* | (2006.01) |
| *B01J 21/18* | (2006.01) |
| *B01J 31/00* | (2006.01) |
| *B01J 35/00* | (2006.01) |
| *C11C 3/04* | (2006.01) |
| *C12N 11/14* | (2006.01) |
| *C11C 3/10* | (2006.01) |
| *B01J 27/02* | (2006.01) |
| *B01J 37/04* | (2006.01) |

(52) U.S. Cl.
CPC ............... *C12N 9/96* (2013.01); *B01J 21/185* (2013.01); *B01J 31/003* (2013.01); *B01J 35/004* (2013.01); *B01J 35/0013* (2013.01); *C11C 3/04* (2013.01); *C11C 3/10* (2013.01); *C12N 11/14* (2013.01); *B01J 27/02* (2013.01); *B01J 37/04* (2013.01); *B82Y 30/00* (2013.01); *Y10S 977/742* (2013.01)

(58) Field of Classification Search
None
See application file for complete search history.

(56) References Cited

U.S. PATENT DOCUMENTS 7,338,590 B1 * 3/2008 Shelnutt et al. ............... 205/628

OTHER PUBLICATIONS

Mei, et al., "Spectroscopy Study of the Immobilized Cellulose of Magnetic Particles Fe3O4" Spectroscopy and Spectral Analysis, vol. 26, No. 5, pp. 895-898 (2006). English-language Abstract included.
Black, K. C. et al., "Gold Nanorods Targeted to Delta Opioid Receptor: Plasmon-Resonant Contrast and Photothermal Agents", Molecular Imaging, 2008, pp. 50-57, vol. 7, No. 1.
Bretschneider, J.C. et al., "Photothermal Control of the Activity of HRP-Functionalized Gold Nanoparticles", Small, 2009, pp. 2549-2553, vol. 5, No. 22.
Chen, J. Y. et al., "Multilayer Gold Nanoparticle-Assisted Protein Tryptic Digestion in Solution and in Gel under Photothermal Heating", Anal.Bioanal. Chemistry (2011), Nov. 2010, pp. 377-385, vol. 399, No. 1.
Chen, W. Y. et al., "Acceleration of Microwave-Assisted Enzymatic Digestion Reactions by Magnetite Beads", Analytical Chemistry, Mar. 2007, pp. 2394-2401, vol. 79, No. 6.
Chou, C-H. et al., "Highly Efficient, Wavelength-Tunable, Gold Nanoparticle Based Optothermal Nanoconvertors", J. Phys. Chem. B, 2005, pp. 11135-11138, vol. 109, No. 22.
Huang, X. et al., "Cancer Cell Imaging and Photothermal Therapy in the Near-Infrared Region by Using Gold Nanorods", J. Am. Chem. Soc., 2006, pp. 2115-2120, vol. 128, No. 6.
Huff, T. B. et al., "Hyperthermic Effects of Gold Nanorods on Tumor Cells", National Institutes of Health Public Access, Dec. 2008, pp. 125-132.
Jeng, J. et al., "Using High-Concentration Trypsin-Immobilized Magnetic Nanoparticles for Rapid In Situ Protein Digestion at Elevated Temperature", Rapid Communications in Mass Spectrometry, 2007, pp. 3060-3068, vol. 21.
Markovic, Z. M. et al., "In Vitro Comparison of the Photothermal Anticancer Activity of Graphene Nanoparticles and Carbon Nanotubes", Biomaterials, 2011, pp. 1121-1129, vol. 32.
Mohamed, M. B. et al., "The 'Lightning' Gold Nanorods: Fluorescence Enhancement of Over a Million Compared to the Gold Metal", Chemical Physics Letters, 2000, pp. 517-523, vol. 317.
Norman, R. S. et al., "Targeted Photothermal Lysis of the Pathogenic Bacteria, Pseudomonas aeruginosa, with Gold Nanorods", Nano Letters, 2008, pp. 302-306, vol. 8, No. 1.

(Continued)

*Primary Examiner* — Anand Desai
(74) *Attorney, Agent, or Firm* — The Webb Law Firm

(57) ABSTRACT

Disclosed is a method for activating a catalyst using the photothermal effects of photothermal nanomaterials, and more particularly to a method of activating a catalyst at a temperature, at which the catalyst has low or no activity, by irradiating a catalyst-photothermal nanomaterial composite with light. The method can activate the catalyst by increasing only the temperature around the nanomaterials without substantially changing the temperature of the reaction medium. A catalyst that generally has high activity at room temperature can be activated even at low temperature. Catalysts having high activity only under mild conditions are immobilized on photothermal nanomaterials so that they have activity even under low temperature and extreme conditions. The invention is useful when a catalyst substrate unstable at room temperature is used or a catalytic product unstable at room temperature is produced.

9 Claims, 9 Drawing Sheets

(56) References Cited

OTHER PUBLICATIONS

Pissuwan, D. et al., "A Golden Bullet? Selective Targeting of Toxoplasma gondii Tachyzoites Using Antibody-Functionalized Gold Nanorods", Nano Letters, 2007, pp. 3808-3812, vol. 7, No. 12.

Robinson, J. T. et al., "Ultrasmall Reduced Graphene Oxide With High Near-Infrared Absorbance for Photothermal Therapy", J Am Chem Soc, May 2011, vol. 133, No. 17. (Abstract only).

Sau, T. K. et al., "Seeded High Yield Synthesis of Short Au Nanorods in Aqueous Solution", Langmuir, 2004, pp. 6414-6420, vol. 20, No. 15.

Slyadnev, M. N. et al., "Photothermal Temperature Control of a Chemical Reaction on a Microchip Using an Infrared Diode Laser", Analytical Chemistry, Aug. 2001, pp. 4037-4044, vol. 73, No. 16.

Takahashi, H. et al., "Gold Nanorod-Sensitized Cell Death: Microscopic Observation of Single Living Cells Irradiated by Pulsed Near-Infrared Laser Light in the Presence of Gold Nanorods", Chemistry Letters, 2006, pp. 500-501, vol. 35, No. 5. (Abstract only).

Yang, K. et al., "Graphene in Mice: Ultrahigh In Vivo Tumor Uptake and Efficient Photothermal Therapy", Nano Letters, 2010, pp. 3318-3323, vol. 10.

* cited by examiner

METHOD FOR ACTIVATING CATALYST USING PHOTOTHERMAL NANOMATERIALS

BACKGROUND OF THE INVENTION

1. Field of the Invention

The present invention relates to a method for activating a catalyst using the photothermal properties of photothermal nanomaterials, and more particularly to a method of activating a catalyst at a temperature, at which the catalyst has low or no activity, by irradiating light into a reaction medium to which either the catalyst and photothermal nanomaterials or a catalyst-photothermal nanomaterial composite has been added.

2. Description of the Prior Art

A catalyst functions to increase the rate of a chemical reaction without itself being consumed in the reaction and is used in a very wide range of applications.

Most catalysts have the highest activity at their optimum temperatures. Enzyme that is a kind of catalyst catalyzes a biochemical reaction in vivo and plays a key role in maintaining the homeostasis of life. Generally, enzymes show high catalytic activities under mild conditions, including room temperature, natural pH and atmospheric pressure. However, chemical catalysts show optimum activity in the show optimum activity temperature range from room temperature to 500° C. or higher, and some of enzymes produced from microbial thermophiles recently found in hot springs or volcanoes show optimum activities at relatively high temperatures close to 100° C. Generally, enzymes produced from thermophiles have the same function as enzymes produced from mesophiles while they stably perform enzymatic reactions under extreme reaction conditions (such as high temperature) in which mesophiles are denatured. Thus, these enzymes have been of industrial interest.

Meanwhile, thermophilic enzymes have good stability, but lack the low-energy and environmentally friendly advantages of enzymes, because they should react at high temperatures. When catalytic reactions occur at higher temperatures, the side reactions of reaction substrates and reaction products are more likely to occur, and a larger amount of energy is consumed. Thus, if a catalyst can react at a very low temperature while maintaining its activity, it will be very useful.

SUMMARY OF THE INVENTION

It is an object of the present invention to provide a method capable of activating a catalyst in a reaction medium at a temperature lower than the optimum activation temperature of the catalyst.

To achieve the above object, the present invention is based on the application of the photothermal effects of photothermal nanomaterials to catalytic reactions, and an object of the present invention is to provide a method of activating a catalyst by adding the catalyst and photothermal nanomaterials to a reaction medium and irradiating the reaction medium with light to generate heat or a method of activating a catalyst by adding a catalyst-photothermal nanomaterial composite to a reaction medium and irradiating the reaction medium with light to generate heat.

DETAILED DESCRIPTION OF THE INVENTION

Figure 1:
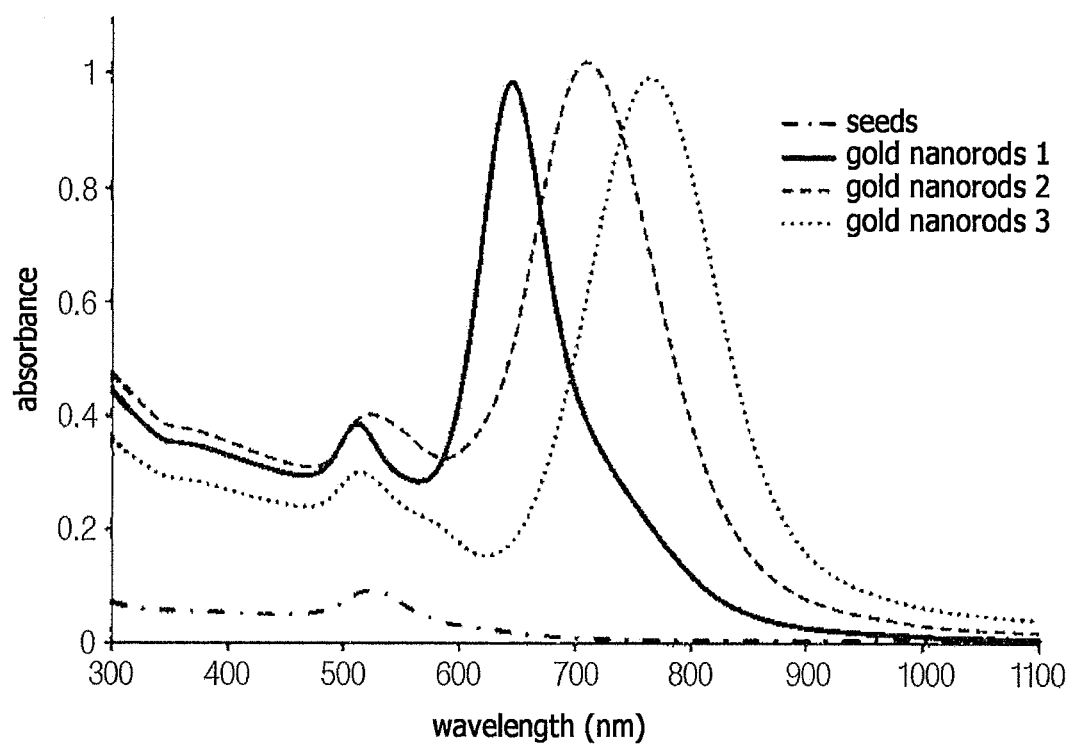
FIG. 1 is a graphic diagram showing that the absorbance spectra of gold seed particles and gold nanorods with different aspect ratios (length/diameter) synthesized using the gold seed particles.

The present invention is based on the application of the photothermal effects of photothermal nanomaterials to catalytic reactions, and provides a method of activating a catalyst by adding the catalyst and photothermal nanomaterials to a reaction medium and irradiating the reaction medium with light to generate heat or a method of activating a catalyst by adding a catalyst-photothermal nanomaterial composite to a reaction medium and irradiating the reaction medium with light to generate heat.

As used herein, the term "catalyst" refers to a substance that increases the rate of a chemical reaction without itself being consumed in the reaction. If a reaction is performed in a reaction medium at a temperature lower than the optimum activation temperature of a catalyst, the catalyst will show low activity. Herein, the expression "catalyst shows low activity" means that the activity is lower than the maximum activity at the optimum activation temperature of the catalyst and is, for example, less than 80%, less than 70%, less than 60% or less than 50% of the maximum activity of the catalyst.

However, when photothermal nanomaterials together with a catalyst are introduced into a reaction medium, the catalyst added to the reaction medium can be activated, because the temperature of the photothermal nanomaterials is increased to the optimum activation temperature of the catalyst due to photothermal effects upon light irradiation.

Thus, the present invention provides a method of activating a catalyst by either adding the catalyst and photothermal nanomaterials or a catalyst-photothermal nanomaterial composite to a reaction medium at a temperature lower than the optimum activation temperature of the catalyst, and then irradiating the reaction medium with light to increase the temperature of the photothermal nanomaterials to the optimum activation temperature of the catalyst. Herein, because the increase in the temperature of the reaction medium is insignificant, the ambient temperature is maintained lower than the optimum activation temperature of the catalyst, and thus the catalytic reaction can be effectively performed even at a temperature lower than the optimum activation temperature of the catalyst.

Meanwhile, the temperature lower than the optimum activation temperature of the catalyst is not specifically limited as long as it is a temperature lower than the optimum activation temperature of the catalyst. For example, it may be a temperature lower than the optimum activation temperature of the catalyst by 5 to 300° C., 5 to 250° C., 5 to 200° C., 5 to 150° C., 5 to 100° C., 10 to 300° C., 10 to 250° C., 10 to 200° C., 10 to 150° C., 10 to 100° C., 20 to 300° C., 20 to 250° C., 20 to 200° C., 20 to 150° C., 20 to 100° C., 30 to 300° C. to 250° C., 30 to 200° C., 30 to 150° C., or 30 to 100° C., but is not limited thereto.

As used herein, the expression "adding the catalyst and the photothermal nanomaterials to the reaction medium" means that the catalyst and the photothermal nanomaterials are introduced into the reaction medium and are simply physically mixed without reacting with each other. Herein, the catalyst and the photothermal nanomaterials can freely move without being immobilized, so that they are randomly close to each other. Thus, when the photothermal nanomaterials emit heat by light irradiation, the temperature of the catalyst present close to the photothermal nanomaterials that emit heat increases to the optimum reaction temperature so that the activity of the catalyst increases.

In one embodiment of the present invention, when the catalyst and the photothermal nanomaterials, which are added to the reaction medium, the photothermal nanomaterials may be added in an amount of 0.01-10,000 parts by weight or 0.01-1,000 parts by weight based on 100 parts by weight of the catalyst.

As used herein, the term "catalyst-photothermal nanomaterial composite" refers to a composite comprising the catalyst immobilized on the photothermal nanomaterials. When the catalyst is immobilized on the photothermal nanomaterials, as the local temperature of the photothermal nanomaterials is increased by light irradiation, the local temperature of the immobilized catalyst also increases. Thus, the temperature of the immobilized catalyst is increased to the optimum activation temperature by the photothermal properties of the photothermal nanomaterials so that the activity of the catalyst is increased.

In one embodiment of the present invention, the catalyst may be a biocatalyst or a chemical catalyst.

As used herein, the term "biocatalyst" refers to a substance that various chemical reactions occurring in vivo. Enzyme is the most typical biocatalyst, and in addition, a microorganism, an animal cell, a plant cell or the like, which contains a specific enzyme, may be used as a catalyst. Meanwhile, as used herein, the term "chemical catalyst" refers to catalytic substances other than the biocatalyst. Examples of the chemical catalyst include chemical substances, such as manganese dioxide, sulfuric acid, sulfuric acid, NaOH, KOH or chitosan.

In one embodiment of the present invention, the catalyst may be enzyme. The enzyme is a protein catalyst that mediates a chemical reaction in a living body, and binds to a substrate to form an enzyme-substrate complex functioning as a catalyst that lowers the activation energy of the reaction. Examples of the enzyme include hydrolases (e.g., amylase, maltase, sucrase, ATPase, etc.) that hydrolyze a substrate in the presence of water ($H_2O$); oxidoredustase (e.g., oxidase or dehydrogenase) that promotes the oxidation reduction reaction of a substance; transferase (e.g., creatine kinase or aminotransferase) that transfers a group of a substrate to other substrates; a substrate degrading enzyme (e.g., catalase or carboxylase); and isomerase (e.g., hexose phosphate isomerase) that changes the atomic arrangement of a substrate molecule.

In another embodiment of the present invention, the catalyst may be a thermostable enzyme. The thermostable enzyme refers to an enzyme stable even at a temperature higher than 50° C. Examples of the thermostable enzyme include, but are not limited to, amylase, glucoamylase or pullulanase, which is isolated from hyperthermophiles and stable at high temperature and shows high activity, thermostable cyclodextrin glycosyltransferase (CGTase), thermostable cellulose, thermostable xylanase, thermostable chitin hydrolase, thermostable protease, thermostable DNA polymerase, thermostable DNA ligase, thermostable glucose isomerase, thermostable alcohol dehydrogenase, thermostable β-galactosidase, and thermostable alkaline phosphatase.

As used herein, the term "photothermal nanomaterials" refers to nanomaterials having the property of generating heat by light absorption.

In one embodiment of the present invention, nanomaterials that show this property may be photothermal metal nanoparticles, carbon nanotubes (CNT), graphene, or graphene oxide.

When the photothermal nanomaterials are photothermal metal nanoparticles, this photothermal property appears mainly in rare metals such as gold, silver or copper. Such metals are widely used in sensor technologies such as localized surface Plasmon biosensors or surface-enhanced Raman sensors. As used herein, the term "photothermal metal nanoparticles" refers to metal nanoparticles that have the property of generating heat by photothermal properties (i.e., light absorption).

As used herein, the term "metal nanoparticles" refers to metal fine particles having a particle size of 1-1000 nm. These metal nanoparticles show optical, electrical and magnetic properties completely different from those of bulky materials, due to the quantum confinement effect in which energy required for electron transfer is changed depending on the size of material, and their large specific surface area. Some metal nanoparticles show photothermal properties, and these metal nanoparticles belong to photothermal nanomaterials. It is known that the photothermal properties of such photothermal metal nanoparticles are controlled by the size and shape of the nanoparticles. Typical examples of photothermal metal nanoparticles include gold or silver nanoparticles which have been used for therapeutic purposes, such as cancer therapy and viral destruction.

Types of nanoparticles that can be used as photothermal nanoparticles include nanotubes, nanoshells, nanorods, nanocages, nano-half-shells or nano pyramids.

Gold nanorods, a kind of photothermal metal nanoparticles, are rod-like gold nanoparticles having a length of several ten to several hundred nanometers and are known to have excellent light absorption properties in the visible region and the near infra-red (NIR) region. Near infra-red (NIR) has a wavelength range of 780 to 2500 nm (https://www.impublications.com/content/introduction-near-infrared-nir-spectroscopy). It was reported that the light absorption wavelength of gold nanoparticles varies depending on the aspect ratio (length/diameter) (Mohamed, M. B. et al., Chem. Phys. Lett. 317, 517-523, 2000). It was already demonstrated by researchers that, when gold nanorods were irradiated with NIR light, the temperature increased to approximately 100° C. within 1 minute (Chou, C. H. et al., J. Phys. Chem. 109, 11135-11138, 2005). Such photothermal properties of gold nanorods have been used for therapeutic purposes, such as cancer therapy and the destruction of pathogenic bacteria and viruses (Huang, X. et al., J. Am. Chem. Soc. 128, 2115-2120, 2006; Huff, T. B. et al., Nanomedicine, 2, 125-132, 2007; Takahashi, H. et. al., Chem. Lett. 35, 500-501, 2006; Black, K. C. et al., Mol. Imaging 7, 50-57, 2008; Pissuwan, D. et al., Nano lett. 7, 3808-3812, 2007; Norman, R. S. et al., Nano Lett. 8 302-306, 2008).

When the photothermal nanomaterials are carbon nanotubes (CNTs), single-walled carbon nanotubes (SWCNTs) or multiwalled carbon nanotubes (MWCNTs) may be used.

CNTs are generally hollow tubes which have a diameter of 1-100 nm and a length of several nanometers (nm) to several ten micrometers (μm) and are comprised of graphite sheets rolled up into cylinders. CNTs show excellent mechanical strength and elasticity and are chemically stable, due to the hard structure of the graphite sheets. In addition, CNTs show various electrical properties, including conductor and semiconductor properties, depending on an angle at which the graphite sheets are rolled up. In addition, they can be advantageously used as advanced materials, because they have a very large surface area due to their nano-sized diameter and high aspect ratio. CNTs are known as nanomaterials having photothermal activity and have received attention particularly because of significantly high quantum-heat energy conversion efficiency together with high capability to absorb near infrared light. When CNTs are irradiated with NIR light, excited electrons in the CNTs are transferred to the valence band while most of produced heat is emitted in the form of heat.

Graphene, a kind of photothermal nanomaterials, is a stacking of monoatomic layers of carbon, has linear energy-momentum dispersion around the Fermi level, and has no band gap. Graphene has excellent properties, including wideband absorption and high thermal conductivity, and thus can be applied to electronic or optical devices. In addition, the graphene surface can bind specifically to various organic/biomaterials by π-π stacking. Studies on the photothermal properties of graphene are in a beginning stage. Similar to CNTs, graphene also absorbs light in the NIR region, and most of energy produced by active migration of electrons is emitted in the form of heat. In recent years, studies on the use of graphene for cancer therapy have been reported (Yang, K. et al., Nano Lett. 10, 3318-3323, 2010; Robinson, J. T. et al., J. Am. Chem. Soc. 133, 6825-6831, 2011; Markovic, Z. M. et al., Biomaterials, 32, 1121-1129, 2011).

A method for preparing the catalyst-photothermal nanomaterial composite is not specifically limited. A method of conjugating any compound onto nanomaterials is well known in the art.

For example, enzyme can be immobilized on nanomaterials by simple adsorption. In addition, a catalyst can be immobilized by covalent bond with photothermal nanomaterials introduced with a functional group. A method of introducing a functional group into nanomaterials is well known to those skilled in the art, and this functional group may be selected from among known functional groups depending on the kind of compound to be introduced.

Specifically, the catalyst-photothermal nanomaterial composite can be obtained by covalent bond either the reaction of an aldehyde-containing crosslinking agent and catalyst with amino groups-functionalized-photothermal nanomaterials or the reaction of an amino-containing catalyst with aldehyde groups-functionalized the photothermal nanomaterials.

As the crosslinking agent, any compound may be used as long as it has an aldehyde group at one end. For example, as the crosslinking agent, polyaldehyde such as glutaraldehyde, dialdehyde starch or succinic acid aldehyde may be used. Preferably, glutaraldehyde is used.

In order for the catalyst to be sufficiently immobilized on the photothermal nanomaterials and to maintain the catalytic activity, the catalyst is preferably used in an amount of 0.1-10 parts by weight based on 100 parts by weight of the photothermal nanomaterials. After the crosslinking reaction, the photothermal nanomaterials immobilized with the catalyst are preferably sufficiently washed with a suitable buffer to remove an insufficiently bound catalyst easy to leave and an excess of the crosslinking agent.

Meanwhile, light is irradiated either into a medium to which the catalyst and the photothermal nanomaterials have been added or into a medium to which the catalyst-photothermal nanomaterial composite has been added, and this light may be sunlight or artificial light (e.g., tungsten light, laser or LED light) and may include light in the infrared region, the visible region or the ultraviolet region.

In one embodiment of the present invention, the optimum activation temperature of the catalyst used in the method for activating the catalyst may be normal temperature.

As used herein, the normal temperature refers to a temperature that is obtained without heating or cooling.

In the following examples, the results of application to HRP enzyme or ADH enzyme are described, but the present invention can be applied to various reactions that involve catalysts. Herein, the term "catalysts" is meant to include all biocatalysts and chemical catalysts that high activities at normal temperature or higher. Enzymes include all enzymes, including various polymerases, various proteases and the like, and biomolecular reactions that involve the enzymes also fall within the scope of the present invention. In the following examples, the use of the photothermal effects of gold nanorods, graphene or CNTs is described by way of example, but the present invention can be applied to all cases in which photothermal nanomaterials are used.

It is obvious to those skilled in the art that the optimum activation temperature of each catalyst or enzyme can vary depending on the kind thereof and that the light absorption wavelength and the increase in temperature upon light irradiation can vary depending on the kind of photothermal nanomaterials.

Hereinafter, the present invention will be described in further detail with reference to examples. However, these examples are for illustrative purposes and are not intended to limit the scope of the present invention. The examples of the present invention are provided to more completely explain the present invention to those skilled in the art.

The following preparation examples are commonly applied to the examples of the present invention.

Preparation Example 1

Synthesis of Gold Nanorods

First, using a CTAB (cetyltrimethyl ammonium bromide) surfactant, gold nanorods were synthesized in an aqueous solution. CTAB was removed from the synthesized gold nanorods which were then used in the next step reaction. Further details are described in Sau and Mrphy, *Langmuir*, 20, 6414-6420, 2004.

To synthesize gold nanorods, gold seed particles are required. Thus, 0.6 ml of 0.01 M $NaBH_4$ was added to a mixed solution of 0.25 ml of 0.01 M $HAuCl_4$ and 7.5 ml of 0.1 M CTAB and then stirred rapidly for 2 minutes. The mixed solution turned light yellowish-brown, and the solution was kept in a water bath at 25° C. for 2 hours, and the gold seed particles were collected. The collected gold seed particles were used to grow gold nanoparticles.

To grow gold nanoparticles, 9.44 ml of 0.1 M CTAB solution, 0.4 ml of 0.01 M $HAuCl_4$ solution and 0.06 ml of 0.01 M $AgNO_3$ solution were sequentially added to a reactor and then stirred mildly. The mixed solution turned light yellowish brown, and when 0.06 ml of 0.1 M ascorbic acid was added thereto, the solution immediately turned colorless. Finally, 0.04 ml of gold seed particle solution was added thereto, stirred mildly for about 10 seconds, and then kept in a water bath at 25° C. for 3 hours or more. The light absorption wavelength of gold nanorods changes depending on the ratio of the cross-sectional diameter to the length, and when the concentrations of the $AgNO_3$, ascorbic acid and gold seed particle solutions are changed, gold nanorods having different light absorption wavelengths are grown. To remove an excess of CTAB from the grown gold nanorods, the gold nanorod solution was centrifuged at 13,000 rpm for about 12 minutes, the supernatant was discarded, and the precipitate was dispersed in triple-distilled water. Then, the dispersion was centrifuged at 10,000 rpm for 10 minutes, the supernatant was discarded, and the precipitate was dispersed again in triple-distilled water. The gold nanorods from which CTAB has been removed were used to make a composite with a catalyst.

The synthesized gold nanorods were analyzed by UV-Vis spectrophotometry and TEM (transmission electron microscopy) to determine the absorption wavelength and particle size thereof. As shown in FIG. 1, the gold seed particles show a peak absorbance only at 513 nm. Using the gold seed particles, three kinds of gold nanorods (GNR1, GNR2, and GNR3) having different absorption spectra were grown. Herein, GNR1 was prepared 0.6 mM $AgNO_3$ solution, 6 mM ascorbic acid solution and 0.04 ml gold seed particle solution, GNR2 was prepared using 0.6 mM $AgNO_3$ solution, 8 mM ascorbic acid solution and 0.04 ml gold seed particle solution, and GNR3 was prepared using 1.2 mM $AgNO_3$ solution, 8 mM ascorbic acid solution and 0.08 ml gold seed particle solution. As shown in FIG. 1, the prepared GNR1, GNR2 and GNR3 showed peak absorbances at 656 nm, 720 nm and 780 nm, respectively. Among them, the gold nanorod GNR3 showing a peak absorbance at 780 nm was selected for subsequent experiments.

Preparation Example 2

Synthesis of HRP (Horseradish Peroxidase)-Gold Nanorod Composite

First, biotin-BSA was immobilized on the synthesized gold nanorods. For this, 100 ul of 0.1 M borate buffer (pH 8.5; containing 0.05% Tween 20) was added to the gold nanorods having a peak absorbance at 780 nm, and the solution was mixed using a pipette. Then, 10 ul of 0.1 mg/ml biotin-BSA (10 mM in PB buffer, pH 7.4) was added to the gold nanorod solution and allowed to react at room temperature for 1 hour, after which 100 ul of 10% BSA in 10 mM $NaHCO_3$ buffer containing 0.05% Tween 20 (pH 8.8) was added thereto and rotated at a very slow speed at room temperature for 1 hour to protect the surface of non-modified gold nanorods. Then, the solution was centrifuged at 4° C. at 10,000 rpm for 20 minutes, the supernatant was removed, and the precipitate was dispersed in 1 ml of 10 mM $NaHCO_3$ buffer (pH 8.8; containing 0.1% BSA and 0.05% Tween 20). As a result, biotin-BSA-immobilized gold nanorod solution (biotin-immobilized gold nanorod) was obtained. Because biotin and streptavidin (STA) have a very high affinity, 10 ul of 0.1 mg/ml STA-HRP in 10 mM phosphate buffer (pH 7.4) was added to the biotin-immobilized gold nanorod solution, allowed to react at room temperature for 1 hour, and then centrifuged at 4° C. at 10,000 rpm for 20 minutes. After removing the supernatant, the precipitate was dispersed in 1 ml of 10 mM $NaHCO_3$ buffer (pH 8.8; containing 0.1% BSA and 0.05% Tween 20). The centrifugation and dispersion process was repeated three times more to remove unreacted compounds, and a purified HRP-gold nanorod composite was collected.

Preparation Example 3

Synthesis of BSA-Gold Nanorod

The surface of gold nanorods has a specific property of easily adsorbing various ligands. Using this property, BSA was adsorbed onto gold nanorods to synthesize a BSA-gold nanorod composite. A specific method for synthesis of the composite is as follows.

To 1 ml of the gold nanorods having a peak absorbance at 780 nm, synthesized in Preparation Example 1, 100 ul of 0.1 M borate buffer (pH 8.5; containing 0.05% Tween 20) was added and mixed using a pipette. Then, 100 ul of 10% BSA in 10 mM $NaHCO_3$ buffer containing 0.05% Tween 20 (pH 8.8) was added to the gold nanorod solution and rotated at a very low speed at room temperature for 1 hour. Then, the reaction was centrifuged at 4° C. at 10,000 rpm for 20 minutes, the supernatant was removed, and the precipitate was dispersed in 1 ml of 10 mM $NaHCO_3$ buffer (pH 8.8; containing 0.1% BSA and 0.05% Tween 20). The centrifugation and dispersion process was repeated twice more to remove unreacted compounds, and a purified BSA-gold nanorod composite was collected.

Preparation Example 4

Synthesis of ADH (Alcohol Dehydrogenase)-Gold Nanorod Composite

First, a polyelectrode was immobilized on the synthesized gold nanorods. To 1 ml of the gold nanorod having a peak absorbance at 780 nm, 5.7 ul of 350 g/L poly(sodium-4-styrenesulfonate) (PSS, Mw. ~70,000 g/mol) and 10 ul of 100 mM NaCl were added and mixed using a pipette. The solution was allowed to react at room temperature for 1 hour, after which it was centrifuged at 4° C. at 10,000 rpm for 10 minutes, the supernatant was removed, and the precipitate was dispersed in triple-distilled water. Then, the centrifugation and dispersion process was repeated once more. To 1 ml of the dispersed PSS-gold nanorod solution, 9.6 ul of 208 g/L poly (diallydimethyl ammonium chloride) (PDDA, Mw. 200,000-350,000 g/mol) and 10 ul of 100 mM NaCl were added and mixed using a pipette, and the mixture was allowed to react at room temperature for 1 hour. Then, the solution was centrifuged at 4° C. at 10,000 rpm for 10 minutes, the supernatant was removed, and the precipitate was dispersed in triple-distilled water. The centrifugation and dispersion process was repeated once more, and a polyelectrode-immobilized PDDA-PSS-gold nanorod solution was collected. To 1 ml of the PDDA-PSS-gold nanorod solution, 2 ul of 1 U/ul ADH was added and allowed to react at room temperature for 1 hour. Then, 100 ul of 10% BSA in 10 mM phosphate buffer containing 0.05% Tween 20 (pH 7.4) was added thereto, and the solution was rotated at a very low speed at room temperature for 1 hour to protect the surface of non-modified gold nanorods. Then, the solution was centrifuged at 4° C. at 9,000 rpm for 15 minutes, the supernatant was removed, and the precipitate was dispersed in 1 ml of 10 mM phosphate buffer (pH 7.4; containing 0.1% BSA and 0.05% Tween 20). The centrifugation and dispersion process was repeated twice more to remove unreacted compounds, and a purified ADH-gold nanorod composite was collected.

Preparation Example 5

Synthesis of HRP-Graphene Composite

In order to examine whether graphene that absorbs light in the NIR region, like gold nanorods, increases the activity of a catalyst by their photothermal properties, HRP was immobilized on graphene in the following manner. 100 ul of 0.1 M borate buffer (pH 8.5) was added to and mixed with 0.1 mg/ml of graphene using a pipette. 10 ul of 1 mg/ml STA-HRP in 10 mM phosphate buffer (pH 7.4) was added to the graphene solution, and the mixture was allowed to react at room temperature for 1 hour. Then, 100 ul of 10% BSA in 10 mM $NaHCO_3$ buffer (pH 8.8) was added thereto and allowed to react at room temperature for 30 minutes to protect the surface of non-modified graphene. Then, the solution was centrifuged at 4° C. at 8,000 rpm for 10 minutes, the supernatant was removed, and the precipitate was dispersed in 1 ml of 10 mM $NaHCO_3$ buffer (pH 8.8; containing 0.1% BSA). The centrifugation and dispersion process was repeated twice more to remove unreacted compounds, and a purified HRP-graphene was collected.

Preparation Example 6

Synthesis of HRP-Carbon Nanotube (CNT)

Because CNTs also absorb light in the NIR region, HRP was immobilized on CNTs in order to demonstrate the photothermal properties of CNTs. Specifically, 100 ul of 0.1 M borate buffer (pH 8.5) was added to and mixed with 1 ml of 0.1 mg/ml single-walled carbon nanotubes (SWCNTs) using a pipette. 10 ul of 1 mg/ml biotin-BSA (in 10 mM phosphate buffer, pH 7.4) was added to the CNT solution and allowed to react at room temperature for 1 hour. Then, 100 ul 10% BSA (in 10 mM $NaHCO_3$ buffer, pH 8.8) was added thereto and rotated at a very low speed at room temperature to protect the surface of non-modified CNTs. Then, the solution was centrifuged at 4° C. at 8,000 rpm for 10 minutes, the supernatant was removed, and the precipitate was dispersed in 1 ml of 10 mM $NaHCO_3$ buffer (pH 8.8; containing 0.1% BSA). As a result, biotin-BSA-immobilized CNT solution was obtained. To the biotin-immobilized CNT solution, 10 ul of 1 mg/ml STA-HRP (in 10 mM phosphate buffer, pH 7.4) was added and allowed to react at room temperature for 1 hour, and the reaction solution was centrifuged at 4° C. at 8,000 rpm for 10 minutes. The supernatant was removed, and the precipitate was dispersed in 1 ml of 10 mM $NaHCO_3$ buffer (pH 8.8; containing 0.1% BSA). This centrifugation and dispersion process was repeated twice more to remove unreacted compounds, and a purified HRP-CNT composite was collected.

Example 1

Activity of HRP-Gold Nanorod Composite at Low Temperature

In order to examine the activity at 4° C. of the HRP-gold nanorod composite obtained by immobilizing HRP (horseradish peroxidase) onto the gold nanorods (synthesized in Preparation Example 1) according to the method of Example 2, the following test was performed.

First, the activity of HRP enzyme of the HRP-gold nanorod composite was measured at room temperature. As a control, the activity of HRP enzyme of the HRP-gold nanorod composite was measured at 4° C.

To measure the enzyme activity, a substrate (such as ABTS) reaction, which involves a change in color, was used. When the enzyme activity was measured at room temperature, colorless ABTS changed to dark green within 5 minutes by the catalysis of hydrogen peroxide and HRP enzyme, and thus a high absorbance at 414 nm was shown (absorbance: 0.821; see the first graph in FIG. 2), but when the enzyme activity was measured at 4° C., the absorbance at 414 nm was lower than that at room temperature (absorbance: 0.293; see the second graph in FIG. 2), because the reaction rate was slower at 4° C. than at room temperature.

Figure 2:
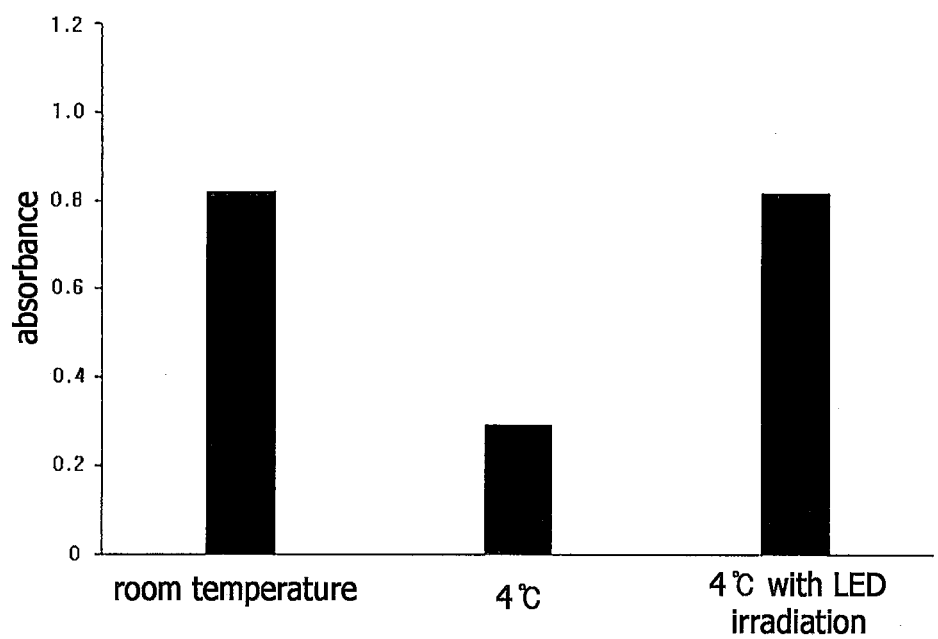
FIG. 2 is a graphic diagram showing the absorbance (absorption wavelength) at 414 nm, obtained in ABTS substrate reactions carried out using an HRP-gold nanorod composite (showing a peak absorbance at 780 nm) under the conditions of room temperature, 4° C., and 4° C. with 800 nm near-infrared light-emitting diode (NIR-LED) irradiation.

However, when the HRP-gold nanorod composite was irradiated with 800 nm-NIR light from a light-emitting diode (LED) at 4° C., activity similar to that shown at room temperature appeared (absorbance: 0.817; see the third graph in FIG. 2).

Herein, light at a wavelength overlapping with the absorption wavelength of the gold nanorods was selected and irradiated into the HRP-gold nanorod composite to examine a substrate reaction. As a result, it was seen that the temperature of the reaction solution did not substantially change, but the activity of the enzyme was increased to the level similar to that at room temperature.

Example 2

Comparison of Activity Between HRP Enzyme and HRP-Gold Nanorod Composite

For comparison, the activity of HRP enzyme alone was measured under the same conditions as Example 1 and was compared with the activity of the HRP-gold nanorod composite.

TABLE 1

| # | Reaction conditions | Absorbance | Reaction medium temperature (° C.) |
|---|---|---|---|
| 1 | HRP, room temperature | 0.878 | 30.2 |
| 2 | HRP, 4° C. | 0.162 | 5.7 |
| 3 | HRP, 4° C. with LED irradiation | 0.282 | 6.1 |
| 4 | HRP-gold nanorod, room temperature | 0.823 | 32.2 |
| 5 | HRP-gold nanorod, 4° C. | 0.095 | 6.7 |
| 6 | HRP-gold nanorod, 4° C. with LED irradiation | 1.004 | 6.7 |

As can be seen in Table 1 above, the activity of HRP enzyme at room temperature was measured at room temperature (#1 in Table 1), an absorbance of 0.878 was shown, but when the activity of HRP enzyme was measured at 4° C. (#2 in Table 1), an absorbance of 0.162 was shown, and when the activity of HRP enzyme was measured at 4° C. with LED irradiation (#3 in Table 3), an absorbance of 0.282. Thus, the increase in activity by LED irradiation was insignificant.

On the other hand, when the HRP activity of the HRP-gold nanorod composite was measured at room temperature (#4 in Table 1), an absorbance of 0.823 was shown, but when the HRP activity of the HRP-gold nanorod composite was measured at 4° C. (#5 in Table 1), an absorbance of 0.095 was shown, whereas when the HRP activity of the HRP-gold nanorod composite was measured at 4° C. after LED irradiation (#6 in Table 6), an absorbance of 1.004 was shown, suggesting that the activity of HRP enzyme was significantly increased.

Figure 3:
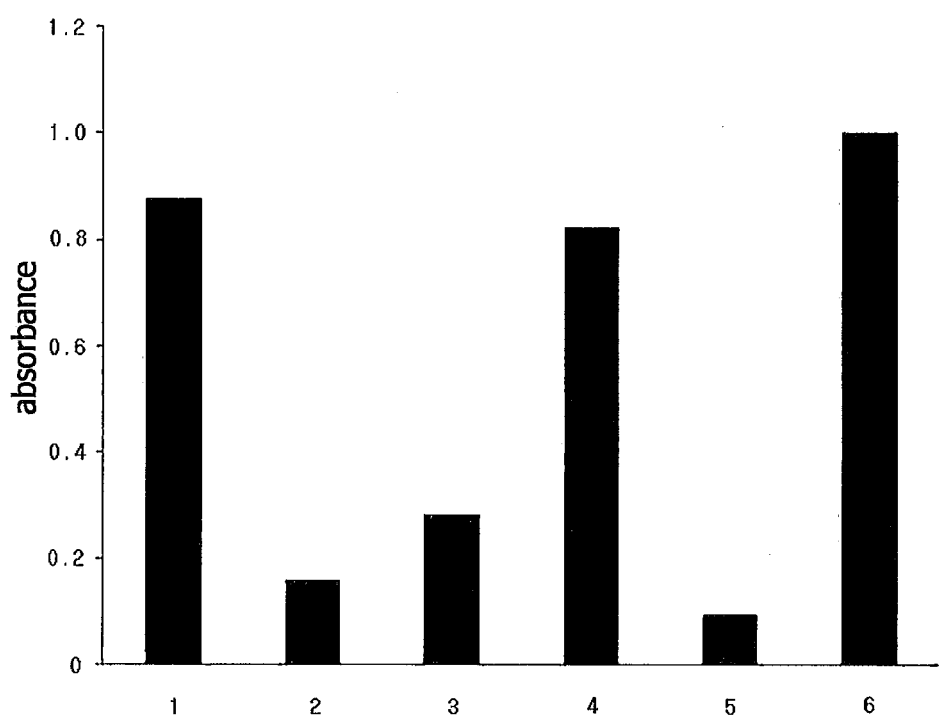
FIG. 3 is a graphic diagram showing the absorbance at 414 nm, obtained in ABTS substrate reactions carried out using HRP and an HRP-gold gold nanorod composite under the conditions of room temperature, 4° C., and 4° C. with NIR-LED irradiation.

The results in Table 1 are shown in FIG. 3.

Example 3

Comparison of Activity Between HRP Enzyme, HRP-Gold Nanorod Composite and BSA-Gold Nanorod Composite/HRP Mixture The HRP activity of a mixture of the synthesized BSA-gold nanorod composite and HRP (weight ratio=1:1) was measured under the same condition as Example and was compared with the activities of HRP enzyme and the HRP-gold nanorod composite.

TABLE 2

| # | Reaction conditions (4° C.) | Absorbance |
|---|---|---|
| 1 | HRP | 0.166 |
| 2 | HRP-gold nanorods | 0.207 |
| 3 | HRP + BSA-gold nanorods | 0.317 |
| 4 | HRP, LED irradiation | 0.262 |
| 5 | HRP-gold nanorod composite, LED irradiation | 0.872 |
| 6 | HRP + BSA-gold nanorod composite, LED irradiation | 1.102 |

As can be seen in Table 2 above, when the activity of HRP enzyme was measured at 4° C. (#1 in Table 2), an absorbance of 0.166 was shown, but when the activity of HRP enzyme was measured after LED irradiation (#4 in Table 2), an absorbance of 0.262 was shown, suggesting that the increase in activity by LED irradiation was insignificant.

On the other hand, when the HRP activity of the HRP-gold nanorod composite was measured at 4° C. (#2 in Table 2), an absorbance of 0.207 was shown, but when the HRP activity of the HRP-gold nanorod composite was measured after LED irradiation (#5 in Table 2), an absorbance of 0.872 was shown, suggesting that the HRP enzyme activity was significantly increased.

In addition, when the HRP enzyme activity of the mixture of HRP and the BSA-gold nanorod composite was measured at 4° C. (#3 in Table 2), an absorbance of 0.317 was shown, but when the HRP enzyme activity of the mixture of HRP and the BSA-gold nanorod composite was measured after LED irradiation (#6 in Table 2), an absorbance of 1.102 was shown, suggesting that the HRP enzyme activity of the mixture was increase compared to that of the HRP-gold nanorod composite.

Figure 4:
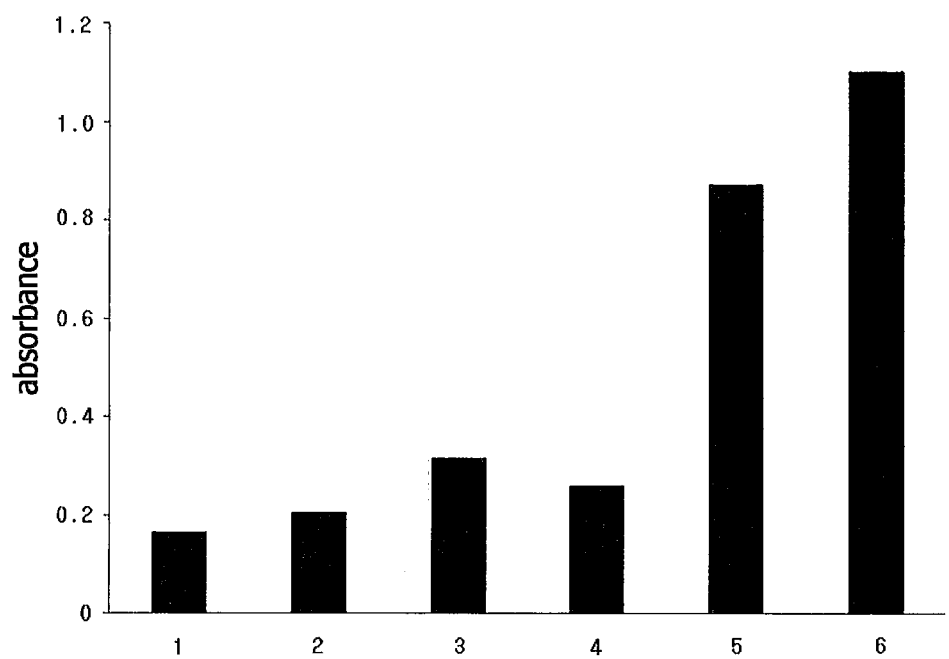
FIG. 4 is a graphic diagram showing the absorbance at 414 nm, obtained in ABTS substrate reactions carried out using HRP, an HRP-gold nanorod composite and a BSA-gold nanorod composite/HRP mixture under 4° C., and 4° C. with NIR-LED irradiation.

The results in Table 2 are shown in FIG. 4.

Example 4

Activity of ADH-Gold Nanorod Composite at Room Temperature

In order to examine the activity at room temperature of the ADH-gold nanorod composite obtained by immobilizing ADH (alcohol dehydrogenase) enzyme on the gold nanorods (synthesized in Preparation Example 1) according to the method of Preparation Example 4, the following test was performed.

First, the activity of ADH enzyme immobilized on the ADH-gold nanorod composite was measured at room temperature. As a control, the activity of ADH enzyme immobilized on the ADH-gold nanorod composite was measured at 40° C.

The ADH enzyme used herein was a $NADP^+$-dependent enzyme that shows the highest enzyme activity at 40° C. To measure the enzyme activity, substrate $NADP^+$ and 2-propanol were used. When the enzyme activity was measured at 40° C., $NADP^+$ was converted to NADPH by the catalytic action of 2-propanol and ADH enzyme, and thus a high absorbance at 340 nm (characteristic wavelength of NADPH) was shown (absorbance: 0.2832; see in the sixth graph in FIG. 5), but when the enzyme activity was measured at room temperature, the absorbance at 340 nm was lower than that at 40° C. (absorbance: 0.0989; see the fourth graph in FIG. 5), because the reaction was slower at room temperature than at 40° C.

However, when the ADH-gold nanorod composite was irradiated with light from 800 nm NIR light from a LED at room temperature, an activity much higher than that without LED irradiation was shown (absorbance: 0.2138; see the fifth graph in FIG. 5), even though it was lower than that at 40° C.

Herein, light at a wavelength overlapping with the absorption wavelength of the gold nanorods was selected and irradiated into the ADH-gold nanorods to examine a substrate reaction. In this case, the temperature of the reaction solution was changed by about 5° C., but the enzyme activity was greatly increased compared to that at room temperature without LED irradiation.

Example 5

Comparison of Activity Between ADH Enzyme and ADH-Gold Nanorod Composite

For comparison, the activity of ADH enzyme alone was measured under the same conditions as Example 4 and compared with that of the ADH-gold nanorod composite.

TABLE 3

| # | Reaction conditions | absorbance | Reaction medium temperature (° C.) |
|---|---|---|---|
| 1 | ADH, room temperature | 0.0709 | 24.3 |
| 2 | ADH, room temperature with LED irradiation | 0.0959 | 27.8 |
| 3 | ADH, 40° C. | 0.2555 | 37.9 |
| 4 | ADH-gold nanorods, room temperature | 0.0989 | 24.25 |
| 5 | ADH-gold nanorods, room temperature with LED irradiation | 0.2138 | 29.1 |
| 6 | ADH-gold nanorods, 40° C. | 0.2832 | 38.2 |

As can be seen in Table 3 above, when the activity of ADH enzyme was measured at 40° C. (#3 in Table 3), an absorbance of 0.2555 was shown, but when the activity of ADH enzyme was measured at room temperature (#1 in Table 3), an absorbance of 0.0709 was shown, and when the activity of ADH enzyme was measured at room temperature after LED irradiation (#2 in Table 3), an absorbance of 0.0959 was shown, suggesting that the increase in absorbance by LED irradiation was insignificant.

On the other hand, when the ADH enzyme activity of the ADH-gold nanorod composite was measured at 40° C. (#6 in Table 3), an absorbance of 0.2832 was shown, but when the ADH enzyme activity of the ADH-gold nanorod composite was measured at room temperature (#4 in Table 3), an absorbance of 0.0989 was shown, whereas when the ADH enzyme activity of the ADH-gold nanorod composite was measured at room temperature after LED irradiation (#5 in Table 3), an absorbance of 0.2138 was shown, suggesting that the ADH enzyme activity was increased twice or more.

Figure 5:
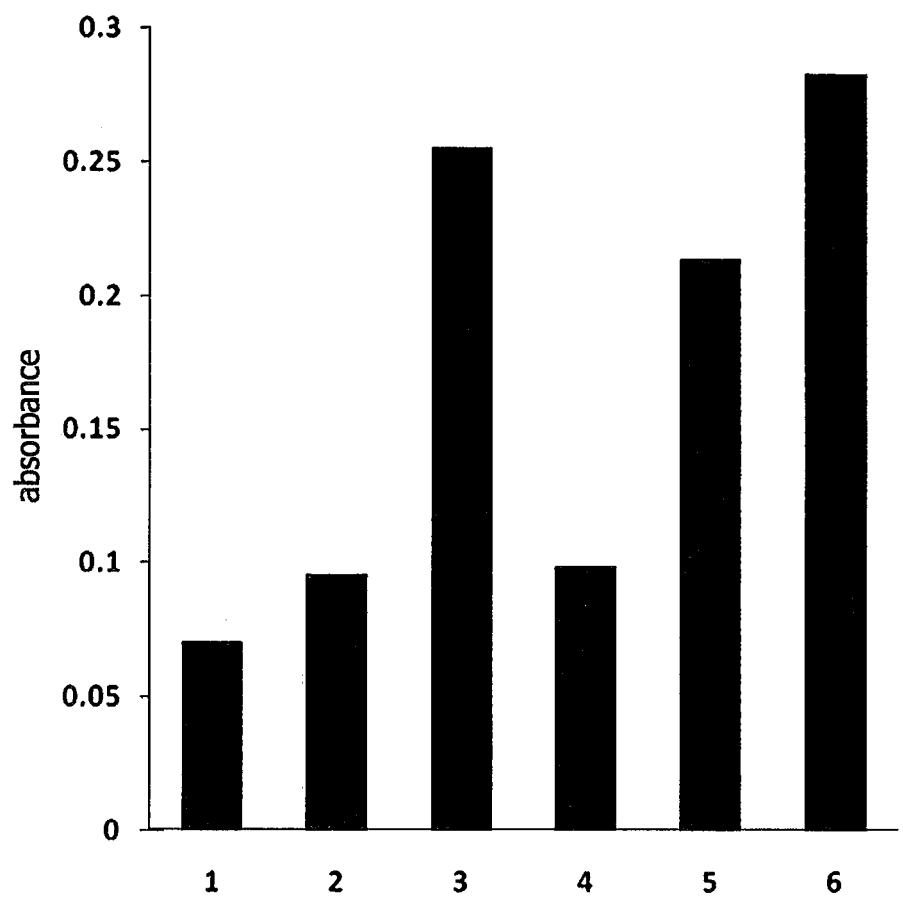
FIG. 5 is a graphic diagram showing the absorbance at 340 nm, obtained in $NADP^+$-to-NADPH conversion reactions carried out using ADH and an ADH-gold nanorod composite under the conditions of 40° C., room temperature, and room temperature with NIR-LED irradiation.

The results in Table 3 are shown in FIG. 5.

Example 6

Comparison of Activity Between ADH-Gold Nanorod Composite and BSA-Gold Nanorod Composite/ADH Mixture The ADH enzyme activity of a mixture of the BSA-gold nanorod composite synthesized in Preparation Example 3 and ADH (weight ratio: 2:1) was compared with the activity of the ADH-gold nanorod composite under the same conditions as Example 4.

TABLE 4

| # | Reaction conditions (room temperature) | Absorbance |
|---|---|---|
| 1 | ADH-gold nanorod composite | 0.102 |
| 2 | ADH-gold nanorod composite, LED irradiation | 0.281 |
| 3 | ADH + BSA-gold nanorod composite | 0.094 |
| 4 | ADH + BSA-gold nanorod composite, LED irradiation | 0.416 |

As can be seen in Table 4 above, when the ADH activity of the ADH-gold nanorod composite was measured at room temperature (#1 in Table 4), an absorbance of 0.102 was shown, but when the ADH activity of the ADH-gold nanorod composite was measured after LED irradiation (#1 in Table 4), an absorbance of 0.281 was shown, suggesting that the enzyme activity increased by about 3 times.

In addition, when the ADH enzyme activity of the mixture of ADH and the BSA-gold nanorod composite was measured at room temperature (#3 in Table 4), an absorbance of 0.094 was shown, but when the ADH enzyme activity of the mixture of ADH and the BSA-gold nanorod composite was measured after LED irradiation (#4 in Table 4), an absorbance of 0.416 was shown, indicating that the enzyme activity increased by four times or more and was higher than that of the ADH-gold nanorod composite.

Figure 6:
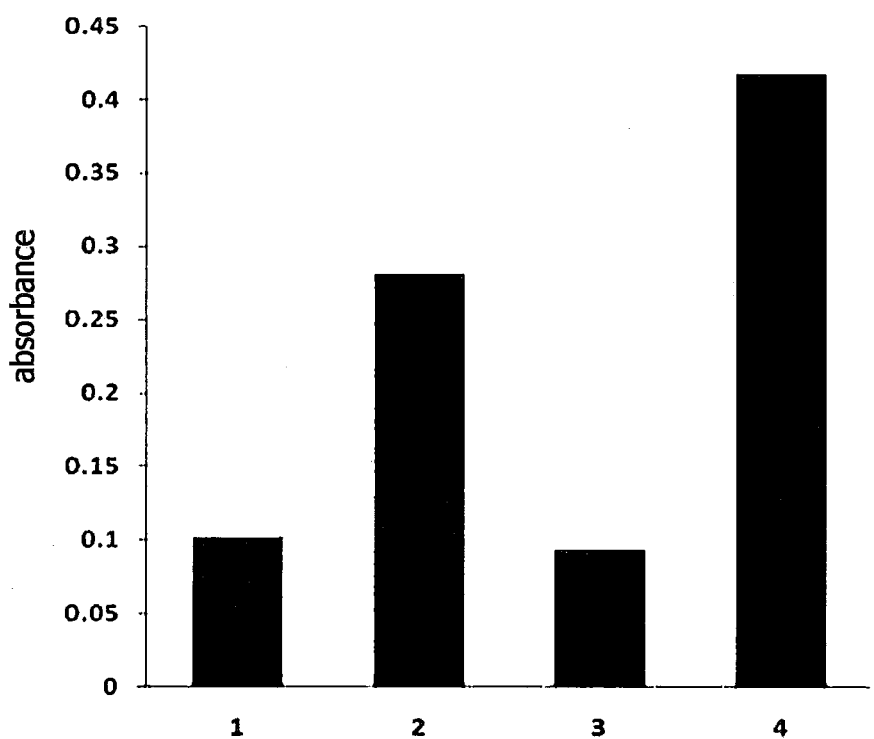
FIG. 6 is a graphic diagram showing the absorbance at 340 nm, obtained in $NADP^+$-to-NADPH conversion reactions carried out using an ADH-gold nanorod composite and a BSA-gold nanorod/ADH mixture under the conditions of room temperature, and room temperature with NIR-LED irradiation.

The results in Table 4 are shown in FIG. 6.

Example 7

Activities of HRP-Graphene Composite and HRP-CNT Composite at Low Temperature

In order to examine the activities at 4° C. of the HRP-graphene composite and the HRP-CNT composite synthesized in Preparation Examples 5 and 6, respectively, the following experiment was performed.

First, the activity of the HRP enzyme immobilized on each of the HRP-graphene composite and the HRP-CNT composite was measured at room temperature. As a control, the activity of the HRP enzyme immobilized on each of the HRP-graphene composite and the HRP-CNT composite was measured at 4° C.

Figure 7:
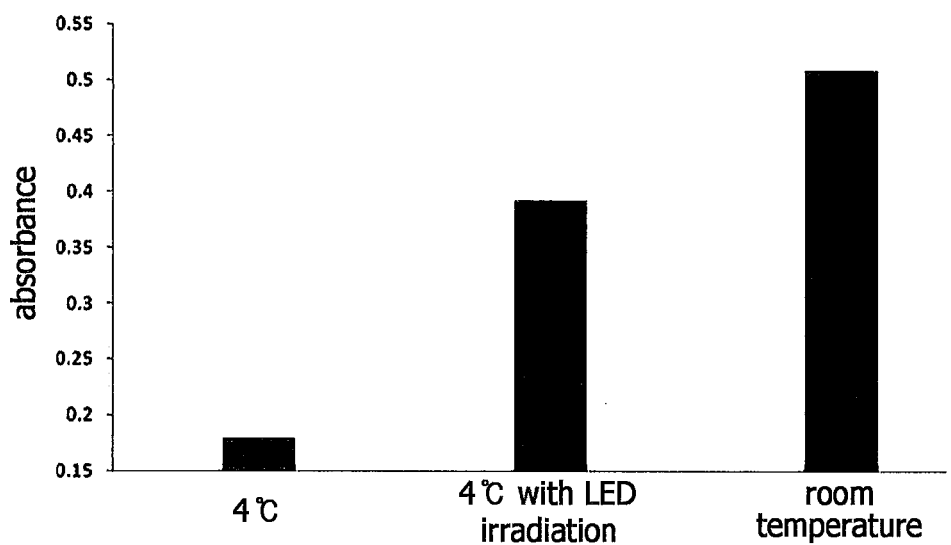
FIG. 7 is a graphic diagram showing the absorbance at 415 nm, obtained in ABTS substrate reactions carried out using an HRP and an HRP-graphene composite under the conditions of room temperature, 4° C., and 4° C. with NIR-LED irradiation.
Figure 8:
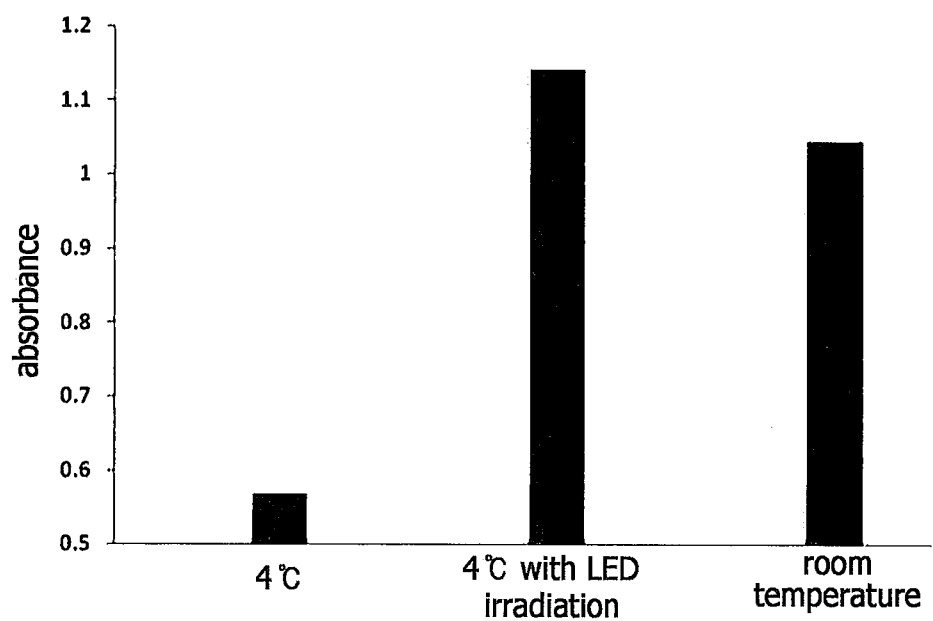
FIG. 8 is a graphic diagram showing the absorbance at 415 nm, obtained in ABTS substrate reactions carried out using an HRP and an HRP-carbon nanotube (CNT) composite under the conditions of room temperature, 4° C., and 4° C. with NIR-LED irradiation.

To measure the enzyme activity, a substrate (such as ABTS) reaction, which involves a change in color, was used. When the enzyme activity was measured at room temperature, colorless ABTS completely changed to dark green within 5 minutes by the catalysis of hydrogen peroxide and HRP enzyme, and thus a high absorbance at 415 nm was shown (for HRP-graphene, absorbance: 0.5092, see the third graph in Table 7; for HRP-CNT, absorbance: 1.0454, see the third graph in FIG. 8), but when the enzyme activity was measured at 4° C., the absorbance at 415 nm was slightly lower than that at room temperature (for HRP-graphene, absorbance: 0.1803, see the first graph in FIG. 7; for HRP-CNT, absorbance: 0.5684, see the first graph in FIG. 8), because the reaction rate was slower at 4° C. than at room temperature.

However, when the HRP-graphene composite was irradiated 800 nm NIR light from a light-emitting diode (LED) at 4° C., the enzyme activity was at least two times higher than that at 4° C. without LED irradiation (absorbance: 0.3924, see the second graph in FIG. 7), even though it was lower than that at room temperature. In the case of the HRP-CNT composite, the enzyme activity of the sample irradiated with LED at 4° C. was higher than that at room temperature (absorbance: 1.1421, see the second graph in FIG. 8).

Example 8

Sulfuric Acid ($H_2SO_4$)/Graphene Mixture and Sulfuric Acid/CNT Mixture for Transesterification of Edible Oil into Biodiesel at 45° C.

Biodiesel is renewable diesel oil extracted from many vegetable oils. Generally, biodiesel is produced by transesterification (in which the ester of any alcohol reacts with another alcohol to produce the ester of the second alcohol and the alcohol of the original alcohol; for example, ethyl acetate and methyl alcohol are produced from methyl acetate and ethyl alcohol) of a natural oil triglyceride (such as vegetable oil or animal fat) with a short-chain alcohol (typically methanol) in the presence of an acid or base catalyst. This reaction occurs stepwise as follows. First, one fatty acid chain is removed to form one monoalkyl ester and a diglyceride, and then the second fatty acid is removed to form two monoalkyl esters and a diglyceride, and lastly, reaction of the third fatty acid occurs. The final products are three monoalkyl esters (biodiesel) and one glycerin. In this Example, edible soybean oil was mixed with methanol at a ratio of 1:10 and subjected to transesterification into biodiesel at 85° C. (for comparison with 45° C.) in the presence of sulfuric acid as an acid catalyst, and the activity of the acid catalyst was examined. After the reaction, the supernatant was 10-fold diluted with acetone and analyzed by HPLC, and the results were compared based on the peak area of biodiesel in the HPLC data.

Specifically, sulfuric acid was added to a mixture of soybean:methanol (1:10) which was then allowed to react at 45° C. for 2 hours, and as a result, the peak area of biodiesel was 1264.351 (#1 in Table 5), indicating that conversion to biodiesel was very insignificant. However, when the reaction was performed at 85° C. for 2 hours, the peak area was 4819.045 (#3 in Table 5), indicating that the amount of biodiesel produced was much more than that at 45° C. Also, when the reaction was performed at 45° C. with LED irradiation, the peak area of biodiesel was 1307.638 (#2 in Table 5), indicating that conversion to biodiesel was also very insignificant.

In order to examine whether the photothermal properties of graphene and CNTs also increase the activity of a chemical catalyst, tests were performed using a sulfuric acid/graphene mixture (1000:1 w/w) and a sulfuric acid/CNT mixture (1000:1 w/w) under the same conditions as the above tests employing sulfuric acid, and conversion to biodiesel was analyzed.

When the sulfuric acid/graphene mixture was used, the peak areas at 45° C. 45° C. with LED irradiation and 85° C. were 1523.109, 3888.268 and 5010.656, respectively (#4, #5 and #6 in Table 5), indicating that the conversion of soybean to biodiesel at 45° C. with LED irradiation was significantly increased compared to that at 45° C. without LED irradiation, even though it was lower than that at 85° C. This suggests that LED irradiation increased the activity of the catalyst.

When the sulfuric acid/CNT mixture was used, the peak areas at 45° C., 45° C. with LED irradiation and 85° C. were 1337.652, 4048.933 and 5047.684, respectively (#7, #8 and #9 in Table 5), indicating that the conversion of soybean to biodiesel at 45° C. with LED irradiation was significantly increased compared to that at 45° C. without LED irradiation, even though it was lower than that at 85° C. This suggests that LED irradiation increased the activity of the catalyst.

TABLE 5

| # | Reaction conditions | Peak area |
| --- | --- | --- |
| 1 | $H_2SO_4$, 45° C. | 1264.351 |
| 2 | $H_2SO_4$, 45° C. with LED irradiation | 1307.638 |
| 3 | $H_2SO_4$, 85° C. | 4819.045 |
| 4 | $H_2SO_4$ + graphene, 45° C. | 1523.109 |
| 5 | $H_2SO_4$ + graphene, 45° C. with LED irradiation | 3888.268 |
| 6 | $H_2SO_4$ + graphene, 85° C. | 5010.656 |
| 7 | $H_2SO_4$ + CNTs, 45° C. | 1337.652 |
| 8 | $H_2SO_4$ + CNTs, 45° C. with LED irradiation | 4048.933 |
| 9 | $H_2SO_4$ + CNTs, 85° C. | 5047.684 |

Figure 9:
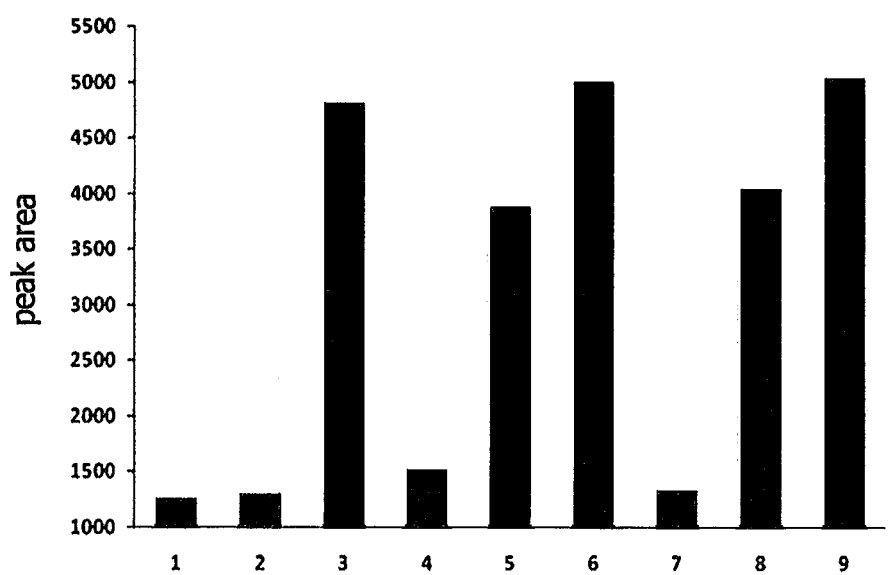
FIG. 9 is a graphic diagram showing the peak areas of biodiesel in HPLC data, which indicate the results of transesterification of edible oil to biodiesel, carried out using sulfuric acid, a sulfuric acid/graphene and a sulfuric acid/CNT mixture under the conditions of 45° C., 45° C. with NIR-LED irradiation, and 85° C.

The results in Table 5 are shown in FIG. 9.

As described above, the method for activating the catalyst according to the present invention can activate the catalyst by increasing only the temperature around the nanomaterials without substantially changing the temperature of the reaction medium. Thus, for example, chemical catalysts or thermostable enzymes that can be activated at high temperature can be activated even at room temperature by light irradiation, thus saving energy.

What is claimed is:

1. A method for activating a catalyst, comprising:
    adding the catalyst and photothermal nanomaterials to a reaction medium having a temperature lower than the optimum activation temperature of the catalyst and increasing the temperature of the photothermal nanomaterials to the optimum activation temperature of the catalyst by light irradiation,
    wherein the light irradiation is near-infrared (NIR) irradiation.

2. A method for activating a catalyst, comprising:
    adding a catalyst-photothermal nanomaterial composite to a reaction medium having a temperature lower than the optimum activation temperature of the catalyst and increasing the temperature of the photothermal nanomaterials to the optimum activation temperature of the catalyst by light irradiation,
    wherein the light irradiation is near-infrared (NIR) irradiation.

3. The method of claim 1 or 2, wherein the catalyst is a biocatalyst or a chemical catalyst.

4. The method of claim 1 or 2, wherein the catalyst is an enzyme.

5. The method of claim 4, wherein the enzyme is a thermostable enzyme.

6. The method of claim 1 or 2, wherein the photothermal nanomaterials are photothermal metal nanoparticles, carbon nanotubes (CNTs), graphene, or graphene oxide.

7. The method of claim 6, wherein the metal nanoparticles are metal nanotubes, metal nanoshells, metal nanorods, metal nanocages, metal nano-half-shells or metal nano pyramids.

8. The method of claim 1, wherein the near-infrared (NIR) irradiation has a wavelength of 780 to 2500 nm.

9. The method of claim 2, wherein the near-infrared (NIR) irradiation has a wavelength of 780 to 2500 nm.

* * * * *